(12) United States Patent
Hull

(10) Patent No.: US 11,305,480 B2
(45) Date of Patent: Apr. 19, 2022

(54) METHODS AND APPARATUS FOR 3D PRINTED HYDROGEL MATERIALS

(71) Applicant: 3D Systems, Inc., Rock Hill, SC (US)

(72) Inventor: Charles W. Hull, Santa Clarita, CA (US)

(73) Assignee: 3D Systems, Inc., Rock Hill, SC (US)

( * ) Notice: Subject to any disclaimer, the term of this patent is extended or adjusted under 35 U.S.C. 154(b) by 0 days.

(21) Appl. No.: 16/843,492

(22) Filed: Apr. 8, 2020

(65) Prior Publication Data

US 2020/0230939 A1 Jul. 23, 2020

Related U.S. Application Data

(62) Division of application No. 15/417,616, filed on Jan. 27, 2017, now abandoned.

(Continued)

(51) Int. Cl.
*B29C 64/112* (2017.01)
*A61L 27/52* (2006.01)
(Continued)

(52) U.S. Cl.
CPC ........... *B29C 64/112* (2017.08); *A61L 27/24* (2013.01); *A61L 27/38* (2013.01); *A61L 27/52* (2013.01); *B29C 35/0805* (2013.01); *B29C 64/106* (2017.08); *B29C 64/129* (2017.08); *B29C 64/188* (2017.08); *B29C 64/194* (2017.08);
(Continued)

(58) Field of Classification Search
CPC ............................ B29C 64/245; B29C 64/112
See application file for complete search history.

(56) References Cited

U.S. PATENT DOCUMENTS 6,136,252 A 10/2000 Bedal et al.
6,270,335 B2 8/2001 Leyden et al.
(Continued)

FOREIGN PATENT DOCUMENTS

JP H051993-158 1/1993
JP 2007-106070 4/2007
(Continued)

OTHER PUBLICATIONS

Hong, Sungmin et al., "3D Printing of Highly Stretchable and Tough Hydrogels into Complex, Cellular Structures", published in Adv. Mater. 2015, 27, 4035-4040, wileyonlinelibrary.com, web.mit.edu [retrieved on Feb. 1, 2016] (7 pages).
(Continued)

*Primary Examiner* — Atul P. Khare

(57) ABSTRACT

There is provided a 3D printing system, methods, and materials for the 3D printing of objects that include a cured hydrogel material, an uncured hydrogel material, and a support material. The cured hydrogel material may define a scaffold for organs or other biological structures. The 3D printing system selectively deposits the hydrogel material and support material, dries the hydrogel material, and selectively applies a catalyst to the hydrogel material to selectively cure the hydrogel material. Once the 3D printing has completed, the uncured hydrogel material may be drained and the support material may be melted or dissolved leaving a scaffold of cured hydrogel material that may be infused with living cells of the desired organ or biological structure.

20 Claims, 1 Drawing Sheet

Related U.S. Application Data

(60) Provisional application No. 62/288,043, filed on Jan. 28, 2016.

(51) Int. Cl.

| | | |
|---|---|---|
| *A61L 27/38* | (2006.01) | |
| *B29C 64/188* | (2017.01) | |
| *C12M 1/00* | (2006.01) | |
| *B29C 64/40* | (2017.01) | |
| *B33Y 70/00* | (2020.01) | |
| *B29C 64/106* | (2017.01) | |
| *C12M 3/00* | (2006.01) | |
| *B29C 64/129* | (2017.01) | |
| *B29C 64/35* | (2017.01) | |
| *B29C 64/386* | (2017.01) | |
| *B29C 64/194* | (2017.01) | |
| *A61L 27/24* | (2006.01) | |
| *B33Y 10/00* | (2015.01) | |
| *B33Y 30/00* | (2015.01) | |
| *B33Y 80/00* | (2015.01) | |
| *B29C 35/08* | (2006.01) | |
| *B29K 105/00* | (2006.01) | |
| *B29L 31/00* | (2006.01) | |

(52) U.S. Cl.
CPC .......... *B29C 64/35* (2017.08); *B29C 64/386* (2017.08); *B29C 64/40* (2017.08); *B33Y 10/00* (2014.12); *B33Y 30/00* (2014.12); *B33Y 70/00* (2014.12); *B33Y 80/00* (2014.12); *C12M 21/00* (2013.01); *C12M 21/08* (2013.01); *B29C 2035/0833* (2013.01); *B29K 2105/0061* (2013.01); *B29K 2995/0056* (2013.01); *B29L 2031/7532* (2013.01)

(56) References Cited

U.S. PATENT DOCUMENTS

| | | | |
|---|---|---|---|
| 6,305,769 B1 | 10/2001 | Thayer et al. | |
| 6,347,257 B1 | 2/2002 | Bedal et al. | |
| 6,596,224 B1* | 7/2003 | Sachs | B29C 41/003 419/6 |
| 6,656,410 B2* | 12/2003 | Hull | B33Y 10/00 264/401 |
| 6,841,116 B2 | 1/2005 | Schmidt | |
| 7,763,272 B2 | 7/2010 | Offerman et al. | |
| 8,197,743 B2* | 6/2012 | Wicker | B29C 64/106 264/401 |
| 8,575,258 B2* | 11/2013 | Stockwell | C08L 91/08 524/478 |
| 8,642,692 B1 | 2/2014 | Stockwell et al. | |
| 8,975,352 B2 | 3/2015 | Stockwell et al. | |
| 9,045,657 B2* | 6/2015 | Lewis | A61L 27/16 |
| 9,242,031 B2 | 1/2016 | Bonassar et al. | |
| 9,604,407 B2 | 3/2017 | Leighton et al. | |
| 2003/0175410 A1 | 9/2003 | Campbell et al. | |
| 2011/0014436 A1 | 1/2011 | Stiles et al. | |
| 2011/0212501 A1* | 9/2011 | Yoo | A61L 27/3886 435/174 |
| 2014/0093932 A1* | 4/2014 | Murphy | C12N 5/0062 435/173.4 |
| 2014/0348940 A1 | 11/2014 | Murphey et al. | |
| 2015/0131074 A1 | 5/2015 | Ebert et al. | |
| 2015/0151487 A1* | 6/2015 | Leighton | B29C 64/40 264/308 |
| 2016/0287756 A1 | 3/2016 | Chapman | |
| 2017/0239886 A1* | 8/2017 | Norikane | C09D 7/20 |

FOREIGN PATENT DOCUMENTS

| | | |
|---|---|---|
| JP | 2015-136895 | 7/2015 |
| WO | 2013123049 | 8/2013 |
| WO | 20130158508 | 10/2013 |
| WO | 2013182547 | 12/2013 |
| WO | 2014004651 | 1/2014 |
| WO | 2016176444 | 11/2016 |

OTHER PUBLICATIONS

Franhofer-Gesellschaft, "Need different types of tissue? Just Print them!", Biotechnica 2013, press release published on Oct. 1, 2013; retrieved from the Internet: https://www.fraunhofer.de/en/press/research-news/2013/oktober/need-different-types-of-tissue-just-print-them-2.html [retrieved on Oct. 26, 2015] (2 pages).
C.Z. Liu et al., Novel 3D Collagen Scaffolds Fabricated by Indirect Printing Technique for Tissue Engineering, J Biomed Mater Res Part B: Appl Biomater 85B, 519-528 (2008) (10 pages); [retrieved from researchgate.net on Feb. 1, 2016].
Lee, Wonhye et al., "ON-Demand Three-Dimensional Freeform Fabrication of Multi-Layered Hydrogel Scaffold With Fluidic Channels," Biotechnology and Bioengineering, vol. 105, No. 6, Apr. 15, 2010, 1178-1186 (9 pages) [retrieved from www.zen-bio.com on Feb. 1, 2016].
Lee, Yeong-Bae et al., "Bio-printing of collagen and VEGF-releasing fibrin gel scaffolds for neural stem cell culture," Experimental Neurology 223 (2010), 645-652 (8 pages); [retrieved from researchgate.net on Feb. 1, 2016].
European communication from the Examining Division of the EPO for European Application No. 17706914.30 dated Nov. 29, 2019 (4 pages).
English Translation of Japanese First Office Action for Japanese Application No. 2018-538152 dated Oct. 2, 2019 (3 pages).
English machine translation of Japanese Application No. JP20050301443 filed on Oct. 17, 2005 (Japanese Publication No. JP2007106070); retrieved from the Internet: URL: https://worldwide.espacenet.com/publicationDetails/biblio?DB=EPODOC&ll=1&ND=3&adjacent=true&locale=en_EP&FT=D&date=20070426&CC=JP&NR=2007106070A&KC=A.
PCT International Search Report for the International Searching Authority for PCT/US2017/015263 dated Apr. 25, 2017 (6 pages).
PCT Written Opinion for the International Searching Authority for PCT/US2017/015263 dated Apr. 25, 2017 (9 pages).
Xiafeng Cui et al: "Direct Human Cartilage Repair Using Three-Dimensional Bioprinting Technology", Tissue Enginnering Part A, vol. 18, No. 11-12, Apr. 18, 2012 (Apr. 18, 2012), pp. 1304-1312 (9 pages)l.
Helena N Chia et al: "Recent advances in 3D printing of biomaterials", Journal of Biological Engineering, Biomed Central Ltd, LO, vol. 9, No. 1, Mar. 1, 2015 (Mar. 1, 2015), p. 4 (14 pages).
English Translation of Indian First Examination Report for Indian Application No. 202018023467 dated Nov. 29, 2021 (5 pages).

* cited by examiner

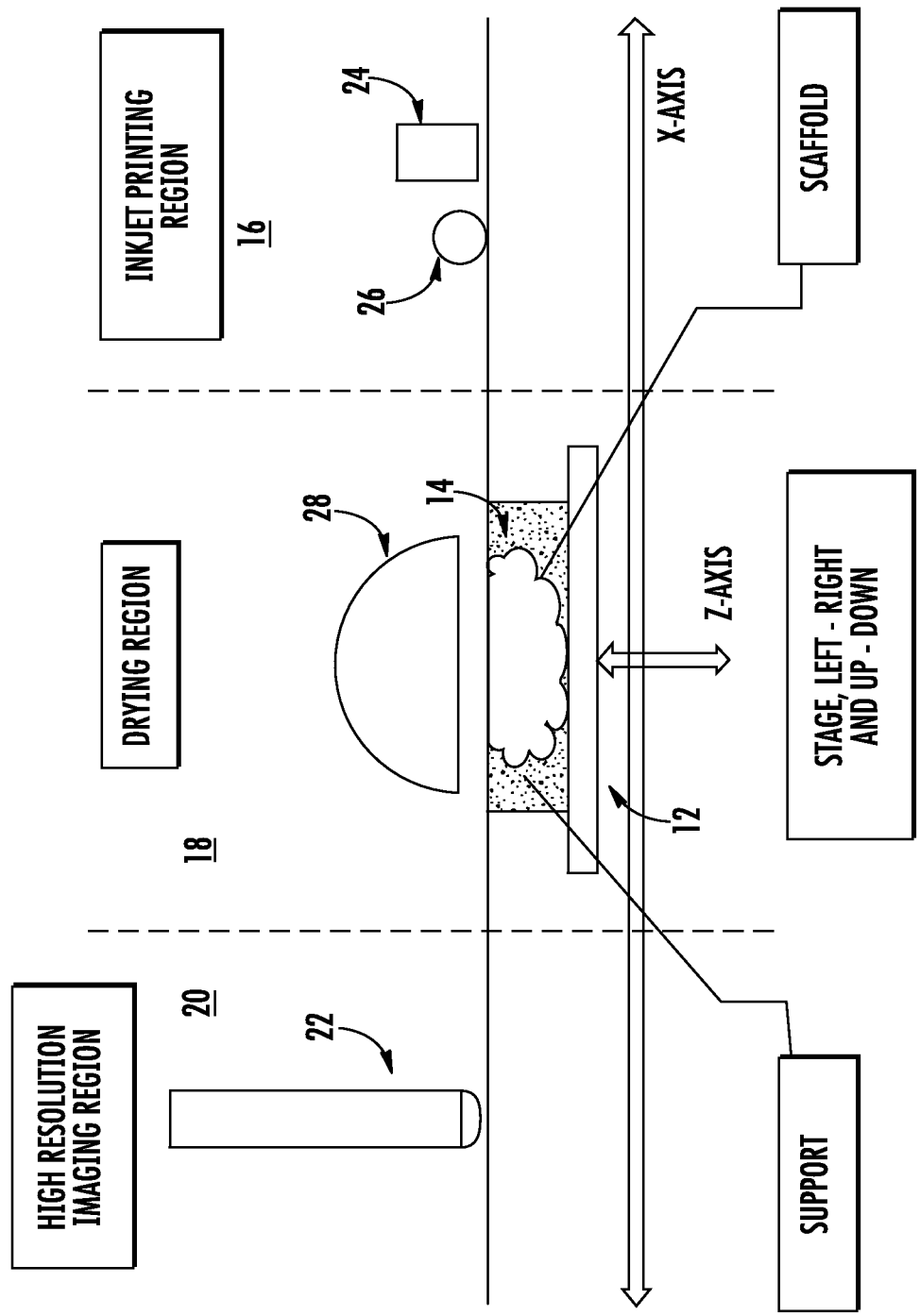

METHODS AND APPARATUS FOR 3D PRINTED HYDROGEL MATERIALS

CROSS REFERENCE TO RELATED APPLICATIONS

This application is a divisional of U.S. application Ser. No. 15/417,616, filed on Jan. 27, 2017, which claims the benefit of U.S. Provisional Patent Application Ser. No. 62/288,043, filed on Jan. 28, 2016, which is hereby incorporated by reference in its entirety.

FIELD OF THE INVENTION

The present invention is related to 3D printing of hydrogel materials, and more particularly, to 3D printing of scaffolding that may be later infused with living cells.

BACKGROUND OF THE INVENTION

A need exists for functional biological structures, such as lungs and other organs, and attempts to date to 3D print such structures or scaffolds have been inadequate.

BRIEF SUMMARY OF THE INVENTION

The various embodiments of the present invention address the above needs and achieve other advantages by providing a 3D printing system, methods, and materials for the creation of 3D printed scaffolding of hydrogel material(s). In one embodiment of the present invention, the 3D printing system comprises: (a) a platform upon which the 3D printed object can be supported during a 3D printing process; (b) a printing portion that selectively deposits one or more hydrogel materials and a support material on the platform; (c) a dryer portion comprising a dryer and through which the platform may pass to dry at least a portion of the material on the platform; and (d) an initiation portion that includes a catalyst source that selectively applies a catalyst to the material on the platform to cause a reaction within at least a portion of the hydrogel material, wherein the catalyst is selectively applied to some, but not all of the exposed hydrogel material on the platform.

Further embodiments include methods for 3D printing a 3D object by (a) selectively depositing a layer of hydrogel material and a support material on a platform; (b) drying at least a portion of the layer of hydrogel material; (c) selectively applying a catalyst to at least a portion of the layer of hydrogel material; and (d) repeating the depositing, drying, and applying for multiple layers of the 3D printed object.

Still further embodiments include 3D printed objects that comprise a scaffold portion comprising a cured hydrogel material, passages within the scaffold portion comprising uncured hydrogel material, and a support structure comprising a support material. The uncured hydrogel may be removed from the cured hydrogel material to provide passages within the scaffold, and the support material may be removed from the scaffold. Therefore, the various embodiments of the present invention provide improvements to the structure, manufacturability, and performance of scaffolds that may be infused with living cells to provide viable biological structure. Still other 3D printed objects can be made with the 3D printing system, methods, and materials of the present invention.

BRIEF DESCRIPTION OF THE SEVERAL VIEWS OF THE DRAWINGS

Having thus described the invention in general terms, reference will now be made to the accompanying drawings, which are not necessarily drawn to scale and are meant to be illustrative and not limiting, and wherein:

FIG. 1 is a schematic side view of a 3D printing system in accordance with one embodiment of the present invention, wherein the 3D printed scaffold, encased in support material, is shown in the drying region between the high resolution imaging region and the ink jet printing region.

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Although apparatus and methods for providing 3D printed hydrogel structures are described and shown in the accompanying drawings with regard to specific types of scaffolds for biological structures, including organs, skin tissue, and the like, it is envisioned that the functionality of the various apparatus and methods may be applied to any now known or hereafter devised 3D printing techniques and materials in which it is desired to provide 3D printed hydrogel objects. Like numbers refer to like elements throughout.

With reference to FIG. 1, a 3D printing system 10 in accordance with one embodiment of the present invention is illustrated. The 3D printing system 10 includes an ink jet printing portion or region 16 that in the illustrated embodiment is similar to solid deposition modeling (SDM) or multi-jet modeling (MJM) systems known in the art, such as U.S. Pat. Nos. 6,136,252; 6,270,335; 6,305,769; 6,347,257; and 6,841,116, the disclosures of which are hereby incorporated by reference in their entirety. The terms "printing portion" and "printing region" are considered equivalent in the present disclosure and are both illustrated as element 16. The platform 12 is moved below one or more ink jet printheads 24 from which the hydrogel material(s) are deposited and the support material(s) are deposited to form a layer of the 3D printed object 14, which in FIG. 1 comprises the scaffold and support. The materials are selectively deposited based upon instructions provided by a controller based upon the design data representing the 3D printed object 14 to be created. The design data is used by the controller to instruct the printhead(s) to deposit each of the hydrogel material and the support material.

The ink jet printhead or printheads 24 of certain embodiments of the present invention comprises a first plurality of orifices through which one or more hydrogel materials can be selectively deposited onto the platform and a second plurality of orifices through which a support material can be selectively deposited onto the platform. The locations of the individual droplets of the respective materials are based upon the design data representing the 3D printed object. In some embodiments, two or more hydrogel materials may be selectively deposited. During deposition of hydrogel and support materials, either after a partial layer, a complete layer, or multiple layers, the platform 12 is moved under a planarizer 26, which in the illustrated embodiment is a heated roller of the type used in the SDM/MJM art. The planarizer removes excess deposited material to ensure layer thickness is correct prior to further deposition of hydrogel and/or support materials or prior to the platform 12 being moved to the drying region 18.

The hydrogel material(s) in some embodiments is a collagen type I or type II (type 1 is used in certain preferred embodiments) or similar material which forms the primary material for the resulting 3D printed object, such as a scaffold. Additional, or alternative, hydrogel materials can be a fibrillin, such as Fibrillar (preferably Type I, II, III, V, XI), any non-Fibrillar, or an elastin. An elastin is used in certain embodiments to provide elasticity to the resulting 3D printed object. Still further embodiments of the present invention use, either alone or as a strengthening material, the hydrogel PEG-alginate, with or without adding $CaSO_4 \cdot 2H_2O$ and with the initiator I-2959, as disclosed in the article by Hong, Sungmin et al. entitled "3D Printing of Highly Stretchable and Tough Hydrogels into Complex, Cellular Structures" published in 2015 in Advanced Materials, the disclosure of which is hereby incorporated by reference in its entirety. Further embodiments of the present invention use alternative hydrogels known in the art or hereafter devised. The particular hydrogel selected for a specific 3D printed object 14 is based upon one or more parameters including, but not limited to, the physical properties of the hydrogel (following the 3D printing process and certain post-processing) and the ability of the hydrogel to undergo photoinitiation without adding or resulting in cytotoxicity or other properties that would make the resulting scaffold or other object unfit for the intended purpose or require relatively extensive post-processing to reduce or eliminate cytotoxicity. The hydrogels in some embodiments of the present invention include initiators that are activated by actinic radiation (the catalyst) as explained below.

The one or more hydrogel materials are dissolved into water in order for the hydrogel to be jettable through the inkjet printhead of the illustrated embodiment. In some embodiments the hydrogel material is dissolved in water at a ratio of about 30:1. Further embodiments of the present invention use alternative ratios of hydrogel material to water in order to achieve the necessary viscosity to be jetted from the particular ink jet printhead(s) or other deposition device, such as a viscosity in the range of 10.0 to 19.0 centipoise, or more preferably in the range of 11.0 to 14.0 centipoise, and still more preferably in the range of 11.3 and 11.8 centipoise (in further embodiments, a viscosity modifier may be included to achieve the desired viscosity). Dissolving the hydrogel material into water serves at least the following two purposes for certain embodiments of the present invention: 1) dilution in water enables the viscosity to be low enough for ink jet printing, and 2) when the excess water is extracted during the drying process (see below) the layer height shrinks from about 25-30 micrometers (typical of ink jet printed layers) to about 0.8-1 micrometers, which is the thickness required to provide the scaffold detail (along the z-axis) necessary for certain biological structures to be effective.

One embodiment of the present invention comprises an ink jet printable hydrogel material comprising a collagen that is solubilized in acetic acid at a pH of about 3 and in a hydrous solution (30:1 water), along with riboflavin as a photoinitiator. The hydrogel material of this embodiment is selectively deposited, from a first set of nozzles of an ink jet printhead, to form layers while a buffer is selectively deposited from a second set of nozzles of the ink jet printhead (or another ink jet printhead) to cause the hydrogel material to gel (at the voxels where the buffer is deposited). The buffer of this embodiment is a phosphate buffered saline ("PBS") that is at a ratio sufficient to move the pH of the deposited collagen from about 3 to between 6 to 8. For example, with a 1× concentration of PBS, the pH of the deposited collagen is raised to about 6.8 and with a 10× concentration of PBS, the pH of the deposited collagen is raised to about 7.4. By raising the pH of the deposited collagen, the collagen self-assembles back into a gel.

Once one or more layers of the hydrogel material, buffer, and support material have been deposited, in accordance with this embodiment of the present invention, the one or more layers are transported to the drying region 18 to remove the excess water from the gel and then the one or more layers are transported to the initiation portion 20 in which high resolution UV (at 254 nm) image exposures selectively crosslink portions of the gelled collagen. This process is repeated for substantially all the layers of the 3D printed object, and then the 3D printed object is post-processed to remove the support material and the non-crosslinked gelled collagen (the non-crosslinked gelled collagen can be removed with an acetic solution). A further post-processing step in accordance with some embodiments of the present invention comprise depositing genipin over the final part (such as a scaffold) to further crosslink the collagen. In further embodiments, glutaraldehyde may be used instead of genipin to post-process the final part; however, because of the cytotoxicity of glutaraldehyde, such post-processed parts for use in biomedical applications, such as scaffolds, may require further washing to remove any cytotoxins prior to use of the parts.

Returning to the illustrated embodiment of FIG. 1, the support material may be a wax material such as a hydrocarbon wax or a hydrocarbon alcohol wax or other wax-based support materials known in the art, such as in U.S. Pat. Nos. 8,575,258; 8,642,692; and 8,975,352, the disclosures of which are hereby incorporated by reference in their entirety. Alternative embodiments of the present invention use support materials, such as other phase change support materials that do not require curing by UV radiation or other actinic radiation.

The support material supports the hydrogel material during the 3D printing process. In some embodiments of the present invention, the support material is printed around the border of each portion of the layer of hydrogel material. This border of support material serves as a 'vat' that contains the cured and uncured hydrogel materials as the 3D printed object is being printed. A region of collagen type I (or similar) material is typically printed between the support border and the scaffold in some embodiments of the present invention. This intermediate region is not exposed with UV or visible light and is not polymerized and thus is retained only by the border of support material and the underlying cured hydrogel material during the 3D printing process.

Once one or more layers of hydrogel material and support material have been selectively deposited in the printing portion 16, the platform 12 is moved along the x-axis, in the embodiment of FIG. 1, to the dryer portion 18 (also referred to as the drying region). A dryer 28 comprising a heat source, a fan, a vacuum, or a combination thereof causes the excess water in the hydrogel material to be removed.

Once the hydrogel has been dried to the proper viscosity, the platform 12 moves along the x-axis again, in the embodiment of FIG. 1, to the initiation portion 20 that includes a catalyst source 22 that selectively applies a catalyst to the material on the platform to cause a reaction within at least a portion of the hydrogel material. In the embodiment of FIG. 1, the catalyst source 22 is a source of actinic radiation, such as UV or visible light, which activates the initiator in the hydrogel material. Sources of actinic radiation include, but are not limited to laser devices, digital mirror devices (DMD/DLP), Grating Light Valve devices (GLV), LEDs, MEMS, mask imaging devices, and any other light emitting device that can selectively project light on a surface. In other embodiments of the present invention, the catalyst source is a catalyst application device that physically deposits a catalyst onto selective portions of the hydrogel material layer.

In certain embodiments of the present invention, the imager is a DMD or DMD array or similar mask imager that is de-magnified so that the pixel spacing is less than one micrometer. For example, if the DMD chip pixel spacing is 5.4 micrometer, the de-magnification is greater than 5.4. Typically the DMD or DMD array is scanned over the layer of hydrogel material and the DMD is programmed to be on or off (or at an intermediate intensity) at each pixel position in the image plane.

For embodiments of the present invention 3D printing scaffolds for biological structures, such as for lungs, the combined ink jet imaging and high resolution mask imaging is programmed to perform such that the collagen type I (or similar) material is formed with very high detail in the regions between the air passages and the blood passages, which require resolution on the order of one micrometer. The overall mechanical strength and elasticity of the scaffold needs to be greater than collagen alone can provide, so that the lung springs back to shape while breathing. Therefore, in some embodiments other stiffer hydrogel like materials need to be interwoven or otherwise incorporated into the base collagen structure. The detail of the tough elastic material or materials is determined by the lower resolution ink jet printing. All the hydrogel materials will be deposited by ink jet printing. Regions within the bulk of the collagen type I (or similar) material will contain the tough elastic material, but none of the tough elastic material will usually be printed in the regions right up to the air and blood passages. The entire cross-section of hydrogel material(s) will be exposed with the UV or visible imager, except for the air and blood passage regions, the regions that will later be infused with living cells, and any other regions left hollow in the scaffold design.

The above process is generally repeated for each layer of the 3D printed object. Once the 3D printing process has completed, the 3D printed object is subjected to a post-processing operation to remove the support material and the uncured hydrogel material. The uncured hydrogel material (that was not initiated by the catalyst) may be drained away from the cured hydrogel either before or after the support material is removed. In some embodiments, the support material may be removed by heat, as generally known in the art, while being careful not to damage the hydrogel material. Still other techniques for removing support material known in the art may be used. The remaining cured hydrogel material is cleaned thoroughly before subsequent use. In the embodiments of the present invention directed to the creation of biological structures, the 3D printed hydrogel material, once properly cleaned, can be infused with living cells of the particular organ or tissue the scaffold was designed for. The design of the scaffold may be based upon the type of biological structure desired, scan data derived from the individual patient for whom the biological structure is intended, and/or other factors that determine the proper shape and structure of the scaffold.

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. It is intended that the present invention cover the modifications and variations of this invention provided they come within the scope of the appended claims and their equivalents. Although specific terms are employed herein, they are used in a generic and descriptive sense only and not for purposes of limitation.

Accordingly, the present invention provides for the production of three-dimensional objects with improved build and support materials. Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. It is intended that the present invention cover the modifications and variations of this invention provided they come within the scope of the appended claims and their equivalents. Although specific terms are employed herein, they are used in a generic and descriptive sense only and not for purposes of limitation.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed:

1. A method of forming a biological scaffold configured to be infused with living cells, the method comprising:
   (1) selectively jetting hydrogel material from one or more printheads onto a build platform according to electronic design data of the scaffold to form a layer of hydrogel having a first thickness of from about 25-30 micrometers;
   (2) drying the layer of hydrogel to remove excess water, thereby reducing a thickness of the layer of hydrogel to a second thickness that is less than the first thickness;
   (3) selectively imaging the dried layer of hydrogel to provide cured portions and uncured portions of the dried layer of hydrogel, the cured portions forming structures of the scaffold on the order of one micrometer; and
   (4) repeating steps (1)-(3) a plurality of times to complete formation of the scaffold.

2. The method of claim 1 wherein the one or more printheads are one or more ink jet printheads.

3. The method of claim 1 wherein the hydrogel material being jetted comprises a hydrogel solubilized in a water-based solution.

4. The method of claim 3 wherein the water-based solution includes the hydrogel solubilized in an acid.

5. The method of claim 4 further comprising selectively depositing a buffer onto the layer of hydrogel so as to increase the pH of the water-based solution to a range between 6 and 8 such that the hydrogel material self-assembles into a gel.

6. The method of claim 4 wherein the acid is acetic acid.

7. The method of claim 1 wherein the hydrogel material being jetted has a viscosity in the range of 10.0 and 19.0 centipoise.

8. The method of claim 1 wherein the hydrogel material being jetted includes one or more hydrogels selected from a list consisting of collagen type I, collagen type II, fibrillin, and elastin.

9. The method of claim 1 wherein the second thickness is from about 0.8-1 micrometers.

10. The method of claim 1 further comprising depositing support material for supporting the layer of hydrogel.

11. The method of claim 10 wherein the support material is printed around a border of the layer of hydrogel.

12. The method of claim 11 wherein repeated layers of the support material are printed around layers of the hydrogel to form a vat.

13. The method of claim 10 wherein the support material includes a hydrocarbon wax.

14. The method of claim 10 wherein the support material is a phase change support material not requiring curing by actinic radiation.

15. The method of claim 1 wherein the biological scaffold is a lung scaffold.

16. A method of forming a biological scaffold configured to be infused with living cells, the method comprising:
  (1) forming a layer of hydrogel having a first thickness on a build platform, wherein said forming comprises jetting a water-based solution comprising a hydrogel material on the build platform and adjusting the pH of the water-based solution to cause the hydrogel material to self-assemble into a gel, and wherein the first thickness is from about 25-30 micrometers;
  (2) drying the layer of hydrogel to remove excess water, thereby reducing a thickness of the layer of hydrogel to a second thickness that is less than the first thickness;
  (3) selectively imaging the dried layer of hydrogel to provide cured portions and uncured portions of the dried layer of hydrogel, the cured portions forming structures of the scaffold on the order of one micrometer; and
  (4) repeating steps (1)-(3) a plurality of times to complete formation of the scaffold.

17. The method of claim 16 wherein adjusting the pH of the water-based solution is via addition of a buffer to the water-based solution.

18. The method of claim 17 wherein the buffer is selectively deposited in areas of the build platform containing the water-based solution.

19. The method of claim 16 wherein the biological scaffold is a lung scaffold.

20. The method of claim 16 wherein the second thickness is from about 0.8-1 micrometers.

* * * * *